(12) United States Patent
Zhou et al.

(10) Patent No.: US 6,506,212 B2
(45) Date of Patent: Jan. 14, 2003

(54) ANATOMICALLY COMPATIBLE POSTERIOR CHAMBER PHAKIC REFRACTIVE LENSES

(75) Inventors: Stephen Q. Zhou, Irvine, CA (US); Igor Valyunin, Laguna Niguel, CA (US)

(73) Assignee: Medennium, Inc., Irvine, CA (US)

( * ) Notice: Subject to any disclaimer, the term of this patent is extended or adjusted under 35 U.S.C. 154(b) by 0 days.

(21) Appl. No.: 09/887,129

(22) Filed: Jun. 22, 2001

(65) Prior Publication Data

US 2002/0004682 A1 Jan. 10, 2002

Related U.S. Application Data

(63) Continuation of application No. 09/611,918, filed on Jul. 7, 2000, now abandoned.

(51) Int. Cl.⁷ .................................................. A61F 2/16
(52) U.S. Cl. ...................... 623/6.38; 623/6.47
(58) Field of Search ...................... 623/6.36, 6.38–6.55

(56) References Cited

U.S. PATENT DOCUMENTS 5,913,898 A * 6/1999 Feingold et al. ............... 623/6
6,224,628 B1 * 5/2001 Cahallan et al. ............ 623/6.4

* cited by examiner

Primary Examiner—Corrine McDermott
Assistant Examiner—Thomas Barrett
(74) Attorney, Agent, or Firm—Frost Brown Todd LLC

(57) ABSTRACT

A phakic refractive lens which conforms to the structure of the eye, particularly to the ciliary sulcus, is disclosed. This lens minimizes stresses of the lens on the interior structure of the eye and eliminates excessive vaulting of the lens which tends to deform the shape of the eye and/or structures in the eye. The lenses comprise an optical body and at least one haptic body. The haptic body(ies) is made up of a first portion adjacent to the optical body, a second portion which extends outwardly from the first haptic portion, and a transition zone between the first and second haptic portions (for example, a groove or score line in the lens surface) which permits the second haptic portion to conform to the shape of the ciliary sulcus of the eye.

19 Claims, 27 Drawing Sheets

ANATOMICALLY COMPATIBLE POSTERIOR CHAMBER PHAKIC REFRACTIVE LENSES

This application is a continuation of U.S. patent application Ser. No. 09/611,918, Zhou and Valyunin, filed Jul. 7, 2000, now abandoned.

BACKGROUND OF THE INVENTION

The present invention relates to intraocular lenses, implanted into the eye for the correction of vision.

A posterior chamber phakic refractive lens (PRL) is surgically implanted behind the iris and in front of the human natural crystalline lens for correcting ametropia, such as myopia, hyperopia, and astigmatism. PRLs should fit inside the eye properly in order to achieve the intended design functions. Because eye sizes are different from one patient to another, various sizes of PRLs must be used for different patients. Even for the same patient, PRLs based on different design principles require different sizes in order to achieve the intended benefit. For example, a PRL of a free-floating design would require that the length of the PRL be approximately same or slightly less than the sulcus-to-sulcus distance (see FIG. 1). In this way, the PRL can be loosely held in place behind the iris and in front of the human natural crystalline lens, hence the free-floating design feature is achieved. On the other hand, a PRL of sulcus-fixed design would require that the length of the PRL is larger than the sulcus-to-sulcus distance (see FIGS. 2, 3). This way, the PRL can be anchored in the sulcus and at the same time it can vault towards the anterior chamber due to the oversized length. The longer the PRL, the stronger the anchoring force and the more the PRL vaults towards the anterior chamber. In the Figures of this application, 1 represents the cornea, 2—the iris, 3—the natural lens, 4—the aqueous humor, 5—the ciliary sulcus, and 6—the phakic refractive lens (PRL).

However, the excessive anchoring force and vaulting due to the oversized length of the PRL may cause a number of undesirable effects on the eye. First, when the PRL is too long, it will cause stress on the ciliary body, zonule, and the natural crystalline lens. Stress on the ciliary body may result in the pupil ovalization. Stress on the zonule may interfere with accommodation in the eye, and stress on the natural crystalline lens may cause capsular opacification or cataract formation. Second, the excessive vaulting may increase the friction force between the iris and the anterior surface of the PRL when the iris dilates or contracts corresponding to light conditions. This increased friction may result in iris chaffing or iris pigment dispersion. Third, the excessive vaulting may decrease the anterior chamber depth. Consequently, it increases the risk of endothelial cell loss. Fourth, excessive vaulting decreases the angle of the anterior chamber. As a result, it slows down the aqueous humor outflow and, therefore, may increase the risk of elevating intraocular pressure, i.e. glaucoma. Lastly, since the ciliary body and zonules are living tissues, they may gradually yield to the stress at the point of PRL contact. The initial gap between the PRL and the natural crystalline lens created by the vaulting of the PRL due to its oversized length may gradually decrease as eye tissues yield to the stress. It may lead to direct contact of the PRL with the natural crystalline lens. This may lead to the capsular opacification of the natural crystalline lens.

For the reasons discussed above, it would be desirable to have an anatomically compatible PRL design, which can be fixated in the sulcus, without the problems caused by the oversized length. The present invention provides PRLs with an "adjustable haptic" design which will prevent the PRL from vaulting excessively. Therefore, it avoids problems otherwise caused by the oversized length of the PRL. Furthermore, the adjustable haptic design allows for a one-size-fits-all design PRL.

BACKGROUND ART

There are a number of patents describing the PRL concept or specific related lens designs. U.S. Pat. No. 4,585,456, Blackmore, issued Apr. 29, 1986, discloses a phakic intraocular lens (IOL) composed of flexible materials positioned against the natural lens of the eye and being held in place immediately adjacent to the natural lens and the ciliary sulcus. It also discloses that surgeons need to select the proper optics for the particular eye. However, there is no disclosure of the phakic IOL's size or the method for selecting the proper size.

Fedorov has several U.S. patents describing new features of phakic refractive lenses for avoiding potential complications. In U.S. Pat. No. 5,480,428, issued Jan. 2, 1996, Fedorov discloses a phakic lens design that has an opening at the center of the optic body. This open hole allows aqueous humor flow through the lens body, thereby preventing IOP (intraocular pressure) elevation. Fedorov, in U.S. Pat. No. 5,258,025, issued Nov. 2, 1993, discloses that post-operative inflammation, caused by the contacting of lens-supporting elements with the ocular tissue, can be prevented by moving the supporting elements to the periphery of the phakic lens. The diameter of the position elements is from about 10 mm to about 10.5 mm. The distance of diametrically opposite ends of the supporting elements is taught to not be less than the diametrical distance between the Zinn's zonules or Zinn's ligaments and is in the range of 11.5 to 12.0 mm (FIG. 4). In the diagram of the IOL, 11 represents the haptics (supporting elements) of the lens. The Zinn's zonules are strong enough to hold the supporting elements in place without causing inflammation. Fedorov, in U.S. Pat. No. 5,766,245, issued Jun. 16, 1998, discloses an IOL for correcting moderate to severe hypermetropia. The length of the IOL is from 10 to 13 mm. However, there is no disclosure of a method for selection of a properly sized PRL for an individual patient. Furthermore, in none of the Fedorov patents was a PRL design disclosed where the haptic length of the PRL can be adjusted for eyes of various sizes.

Kelman, in U.S. Pat. No. 4,769,035, issued Sep. 6, 1988, discloses a surgical procedure for correction of the eyesight of a human eye by implanting an artificial lens between the iris and anterior surface of the human lens. It is a multi-step procedure including the following two steps. First, the patient's refractive error is measured so that the artificial lens can be properly selected with desirable optical power for the patient. Second, the shape of the anterior surface of the patient's natural lens is determined so that the artificial lens can be selected to have its posterior surface shape conforming to the anterior surface of the patient's natural lens. In other words, the posterior surface of the optic portion of the artificial lens is in substantial face-to-face contact with the anterior surface of the patient natural lens. Kelman also pointed out that ultra-sonography technology (A scan or B scan) can be used for determining the shape of the patient's natural lens and that the longitudinal length of the artificial lens is approximately 13 mm. Nevertheless, Kelman's lenses are not designed for adjusting their overall haptic length for fitting various eye sizes.

Lastly, Valunin's U.S. Pat. No. 6,015,435, issued Jan. 18, 2000, discloses a PRL and a method of fitting the PRL between the iris and the anterior surface of the human natural lens. The PRL's size and dimensions are selected in such a way that the haptic bodies of the PRL cannot contact the outermost circumference of the ciliary sulcus of the wearer at the same time. Among other disclosures, Valunin indicates that the maximum diagonal haptic body dimension is preferably from about 10.5 mm to about 11.5 mm (FIG. 5). However, Valunin is silent on whether the haptic design is size adjustable.

Accordingly, there is a need for an anatomically compatible PRL design where the haptics, when needed, can be adjusted for fitting eyes of various sizes. In other words, PRL designs of the present invention can be size adaptive according to the dimensions of the individual eye. These lenses avoid the problems otherwise caused by oversized haptic length in a relatively small eye.

SUMMARY OF THE INVENTION

The present invention relates to an anatomically compatible phakic refractive lens for the correction of ametropia, structurally adapted to be positioned in the posterior chamber of the eye, comprising:
(a) an optical body having a diameter of from about 3 to about 7 mm; and
(b) at least one haptic body which comprises:
  (i) a first portion which is attached to and extends from said optical body, has a diagnostic distance of from about 8 to about 11 mm, and which is structurally adapted to conform in whole or in part to the anterior surface of the natural crystalline lens of the eye;
  (ii) a second portion which extends outward from the outer edge of said first portion, and has a diagnostic distance of from about 11 to about 14 mm; and
  (iii) a transition zone between said first portion and said second portion structurally adapted to permit said second portion to conform to the shape of the ciliary sulcus of the eye.

In preferred lenses, there are two haptics which extend in opposite directions from the optical body; the transition zone includes a score or groove in the lens surface or includes a change in the radius of curvature of the posterior surface of the haptic; the posterior surface of the first haptic body has the same radius of curvature as the posterior surface of the optical body; and the second haptic portion of the lens may be bent relative to the first haptic portion.

DETAILED DESCRIPTION OF THE INVENTION

The object of the present invention is to use PRLs having anatomically compatible design for the correction of ametropia, such as myopia, hyperopia, and astigmatism. Another object of the present invention is to design a PRL in which at least a portion of the PRL haptics will contact and rest on the zonules and/or ciliary body, but will not cause excessive vaulting, which otherwise may lead to complications. In order to understand how this size adjustable haptic design works, the following examples are given for the purpose of illustration, but not to limit the scope of the present invention.

Figure 6:
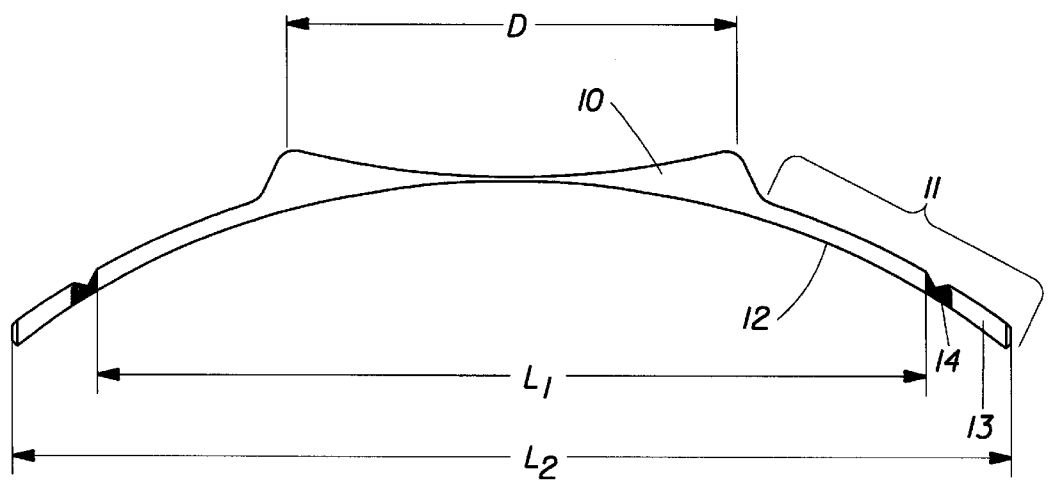
FIG. 6 is a side view of a PRL of the present invention.
Figure 7:
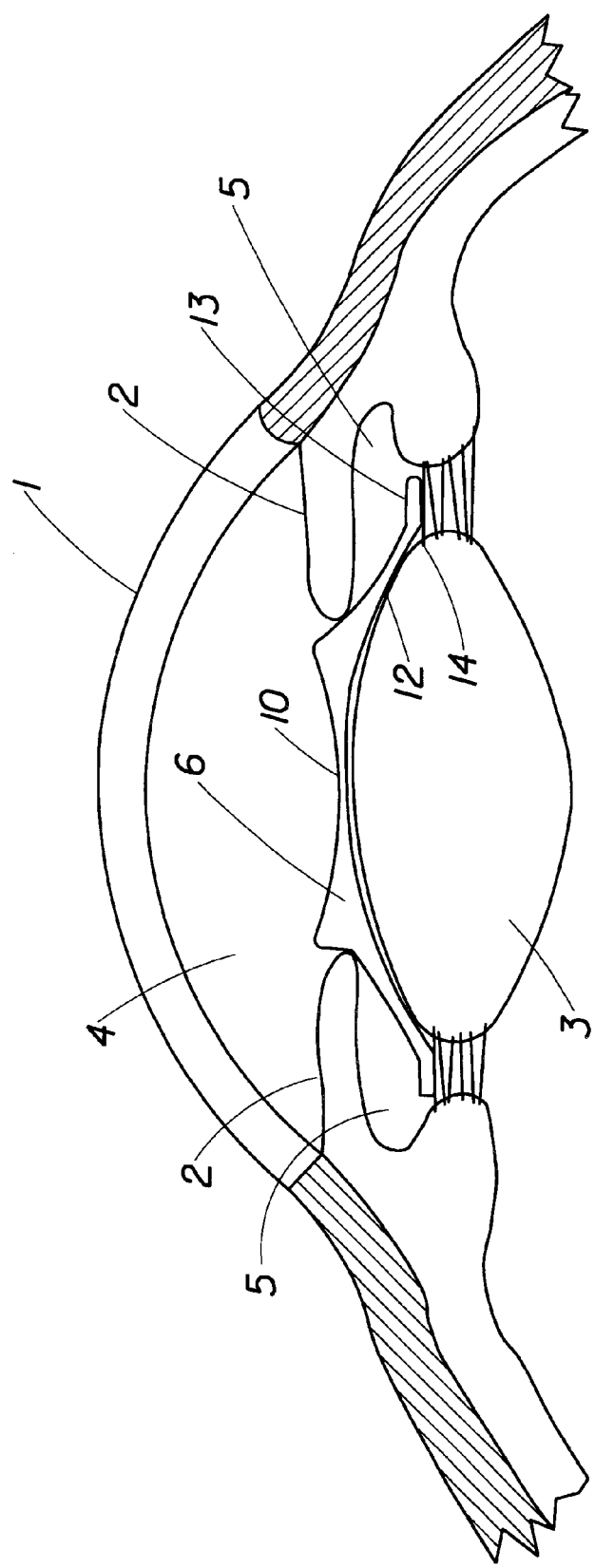
FIGS. 7 and 8 are schematic views of the structure of the eye showing the placement of PRL's of the present invention in the eye.
Figure 8:
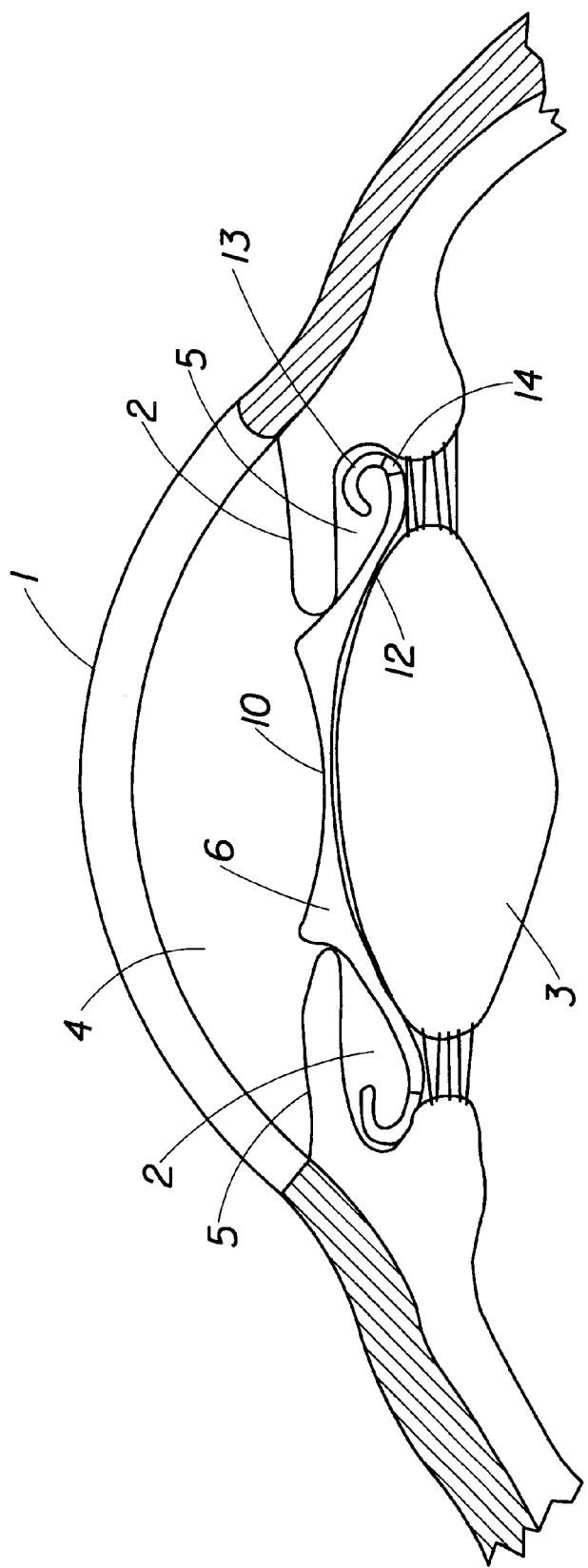

The anatomically compatible PRL design of the present invention comprises, in its broadest sense, an optical body (10) and a haptic body (11). As shown in FIG. 6, the optical body has a diameter (D) in the range of about 3 to about 7 mm, preferably from about 4.5 to about 5.5 mm. The haptic body is further divided into a first portion of the haptic body (12), a second portion of the haptic body (13), and a transition zone (14) between the first portion and the second portion of the haptic body. In a general sense, the optical body and the haptic body of the lens are either co-planar or situated in parallel planes. The first portion of the haptic body (12) is attached to and extends from the edge of the optical body. The radius of the curvature for the posterior surface of the first haptic portion is substantially the same as that for the optical body and is in the range of about 8 mm to about 12 mm, preferably from about 9.5 mm to about 10.5 mm. The first portion of the haptic body has a diagnostic distance ($L_1$), which is approximately equal to the diameter of the natural crystalline lens and is in the range of from about 8 mm to about 11 mm, preferably from about 9 mm to about 10 mm, depending on the patient's age and eye sizes. The second portion of the haptic body (13) is the extension of the first portion of the haptic body via the transition zone. The diagnostic distance ($L_2$) of the second portion of the haptic body must be larger than the diameter of the natural crystalline lens and is generally in the range of about 11 mm to 14 mm, preferably from about 12 to about 13.5 mm. This second portion of the haptic body is designed for being adjustable for various eye sizes to avoid the excessive vaulting. The second portion can generally fold, bend or roll, and it is this ability which provides the size adjusting nature of the lens. The ability to adjust the effective overall length of the PRL in these embodiments is achieved by flattening of the second portion of the haptic body on zonules (FIG. 7) and by rolling into the sulcus (FIG. 8).

Figure 14:
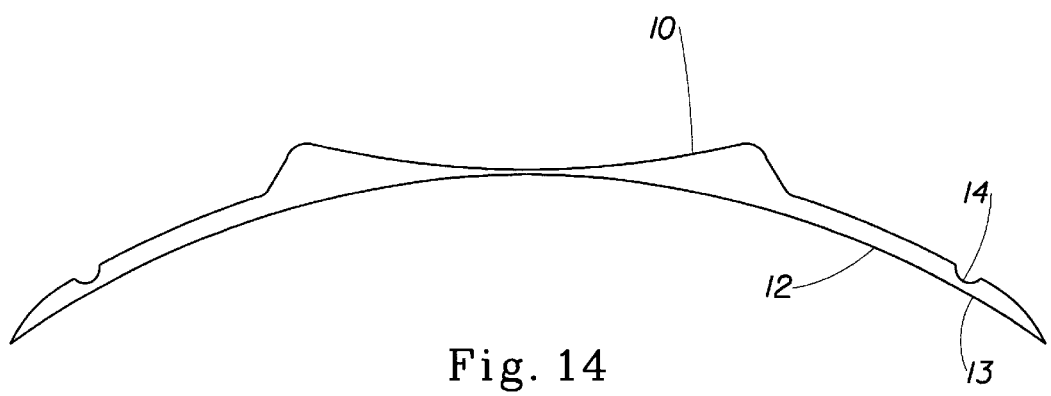
Figure 16:
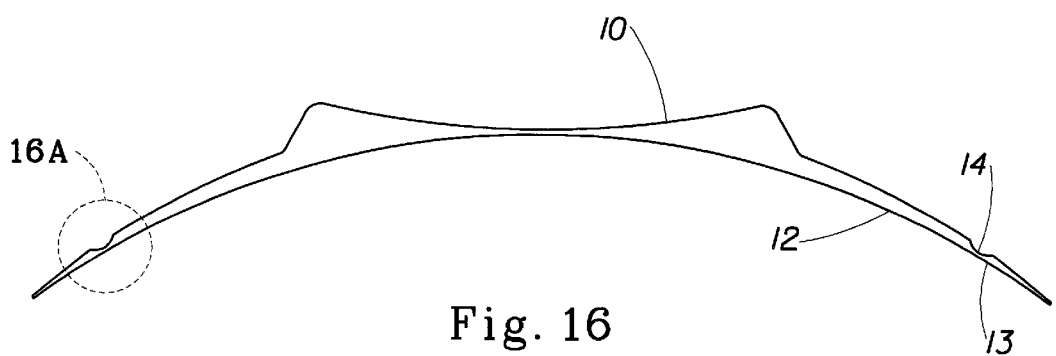
Figure 16A:
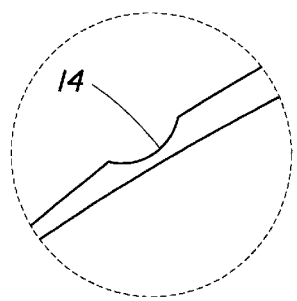
Figure 17:
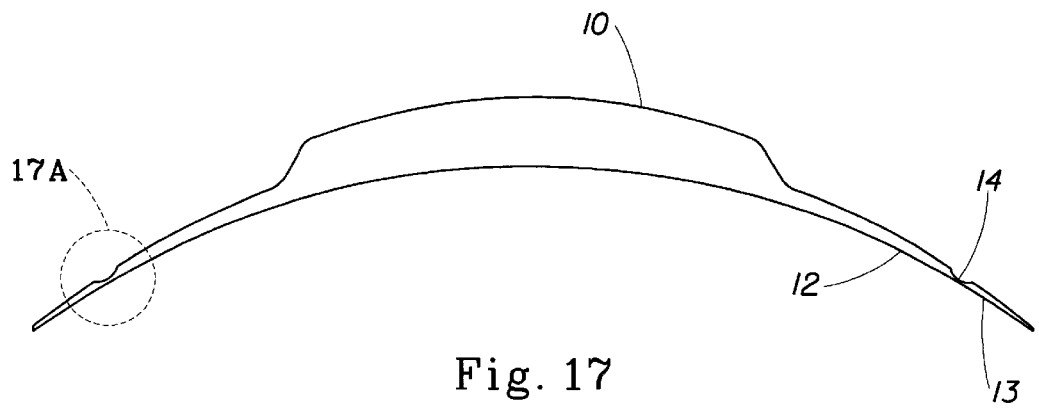
Figure 17A:
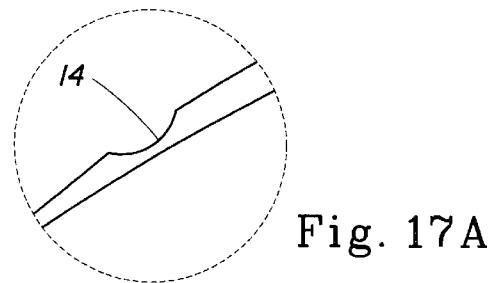
Figure 18:
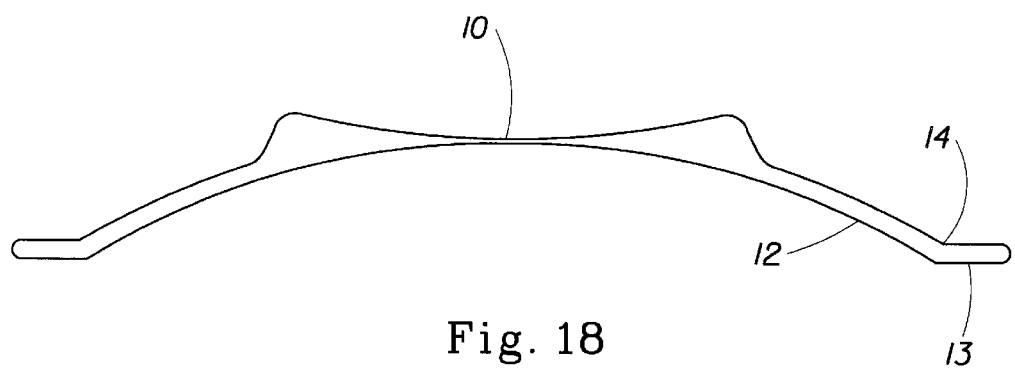
Figure 19:
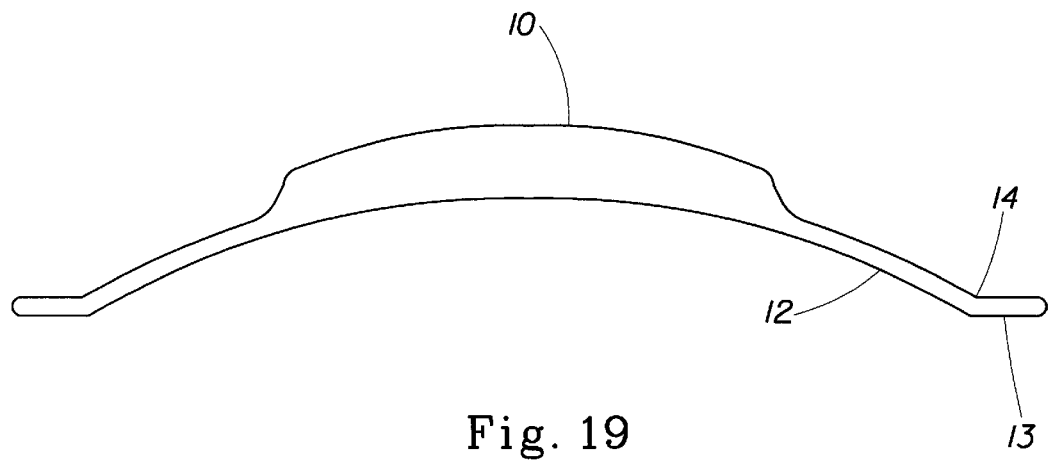
Figure 20:
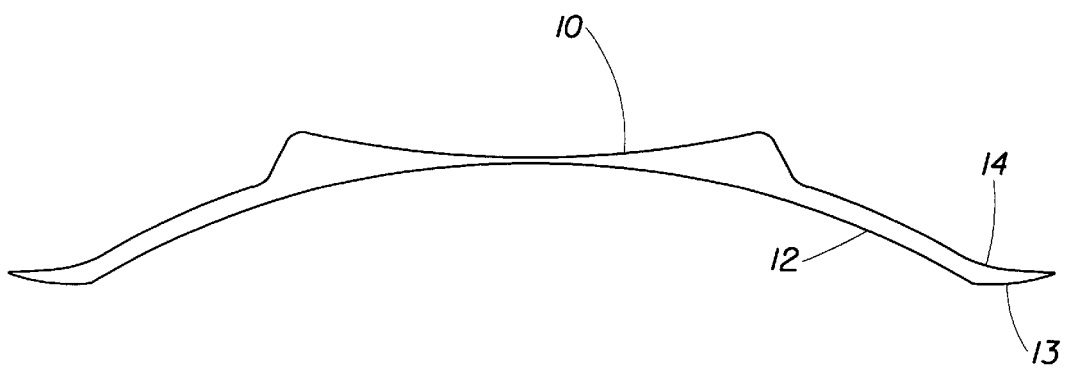
Figure 21:
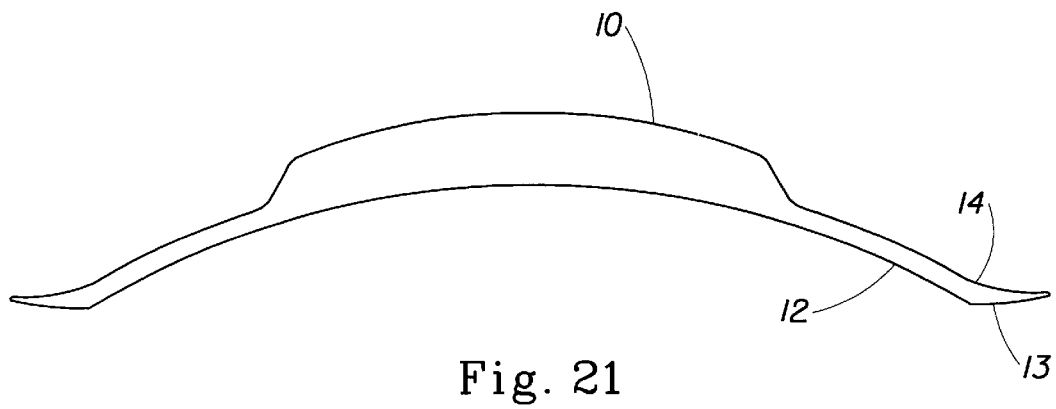
Figure 22:
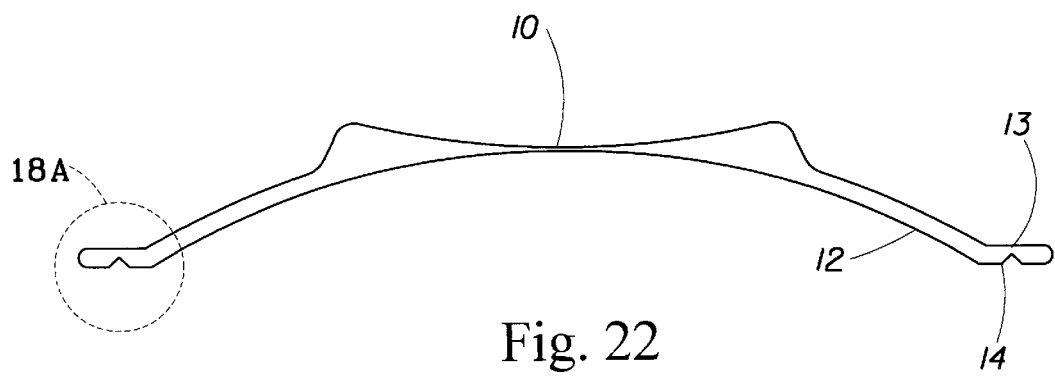
Figure 22A:
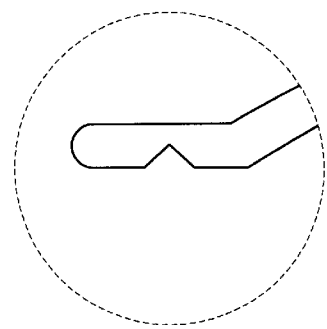
Figure 23:
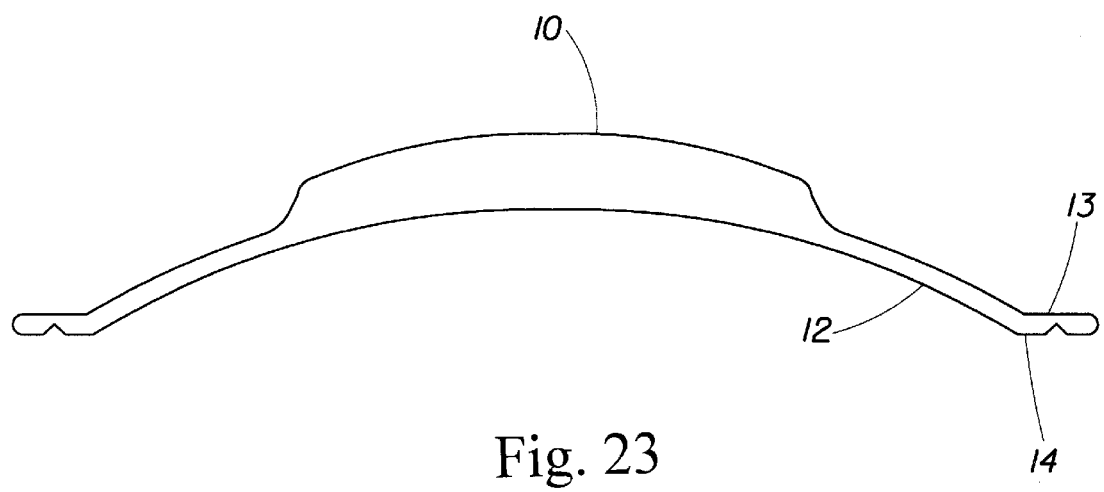

In order to guide the flattening or rolling motion, there preferably needs to be a structural change from the first haptic portion to the second haptic position in the transitional zone (14). This change can be, for example, a score or a groove in the surface of the lens, or a change in the radius of curvature in the posterior surface of the haptic. The purpose of this change is to allow the second haptic portion to conform to the surface of the ciliary sulcus. In preferred embodiments, the second haptic posterior can bend relative to the first. For example, the transition zone can be the V-shape cut in FIGS. 6, 9, 11, 12, or some other cut or groove designs, such as the ones shown in FIGS. 14, 16, and 17. Such grooves, scores or cuts allow the second haptic portion to bend relative to the first portion. Alternatively, the transition zone can be still other kinds of designs (e.g., changes in shape or radius of curvature between the first and second haptic portions) that guide the second portion of the haptic body to rest flatly on zonule and roll into the sulcus (FIGS. 18–23). In these designs, the guiding structure is the change in direction (slope, radius of curvature) of the second portion of the haptic body from the first portion of the haptic body. The transition zone is the place where the first portion of the haptic body changes its curvature. In addition to this curvature change, the transition zone can additionally include a cut, score or groove. For example, the V-shape cut on the second portion of the haptic body shown in FIGS. 22 and 23 is for guiding part of the second portion of the haptic body to roll into the sulcus (FIG. 8). Those skilled in the art understand that there is a void space in and around the ciliary sulcus. When the diameter of the second portion of the haptic body ($L_2$) is larger than the sulcus-to-sulcus distance, the second portion of the haptic body rolls into the sulcus, as shown in FIG. 8.

Figure 9:
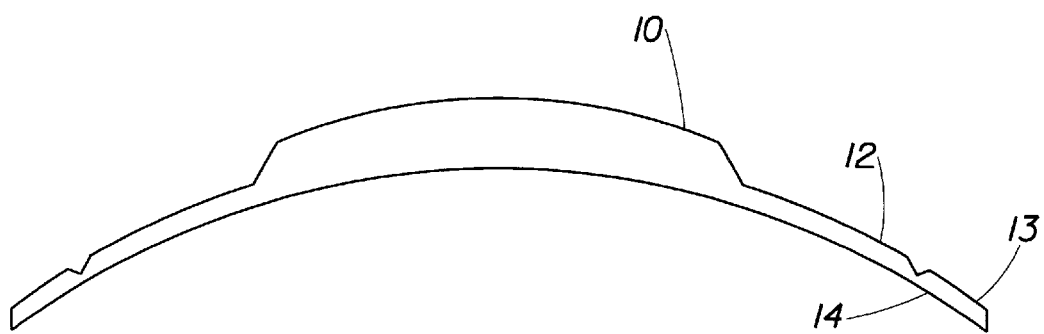
FIGS. 9, 11, 12, 14, and 16–23 are side views of various embodiments of the PRL of the present invention.
Figure 10A:
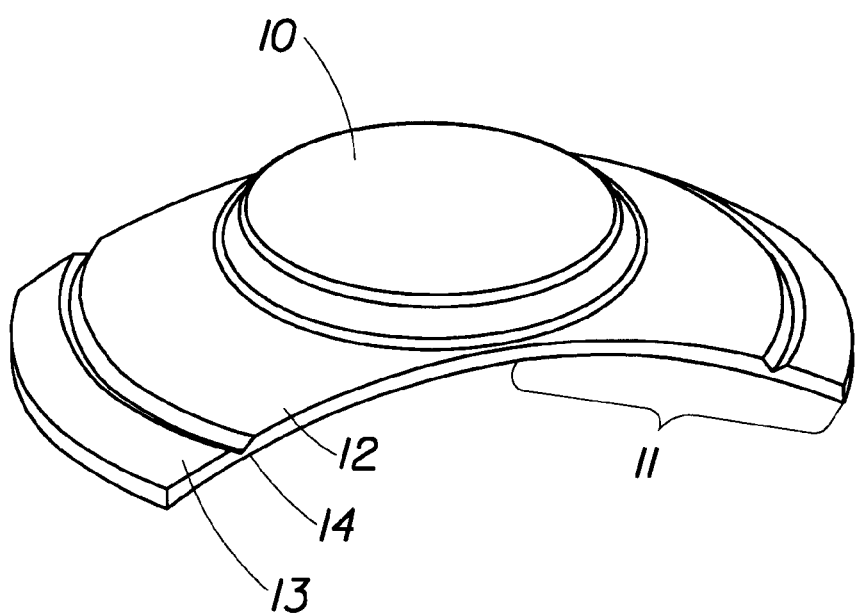
FIGS. 10, 13, 15, 24 and 25 are perspective top views of various embodiments of the PRL of the present invention.
Figure 10B:
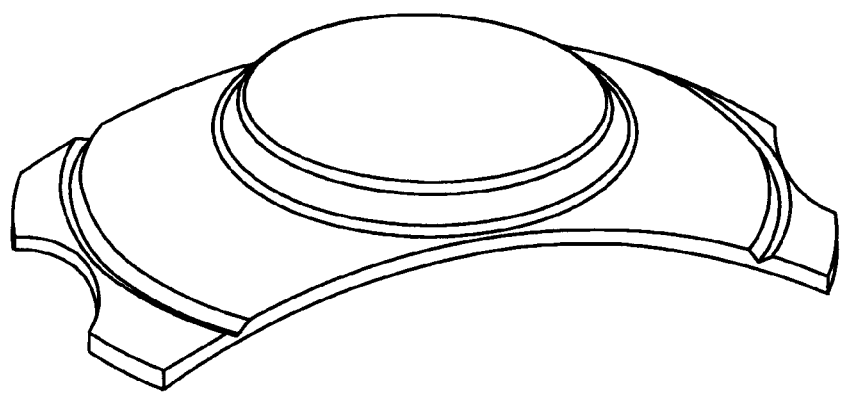
Figure 11:
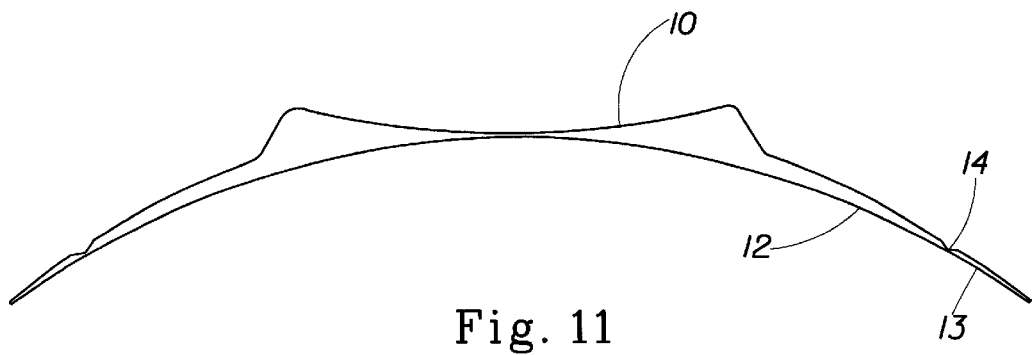
Figure 12:
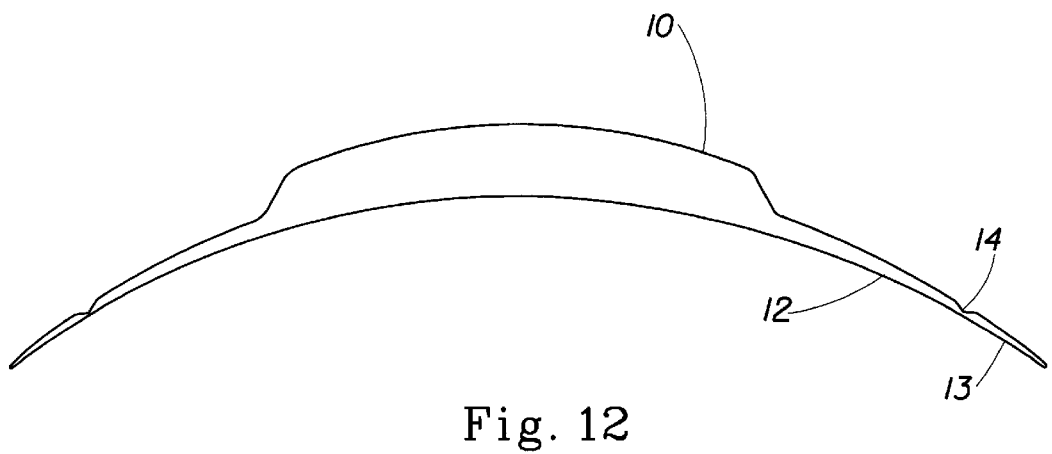
Figure 13:
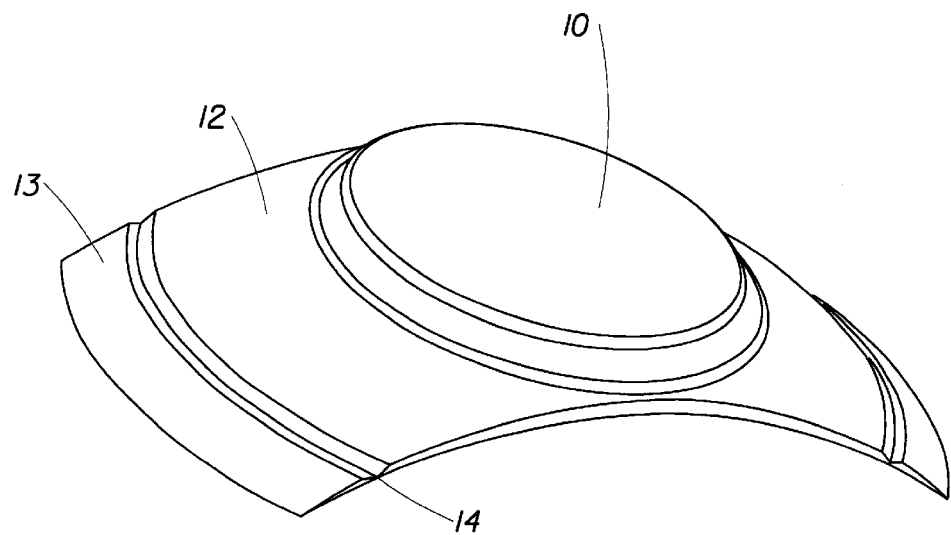
Figure 15:
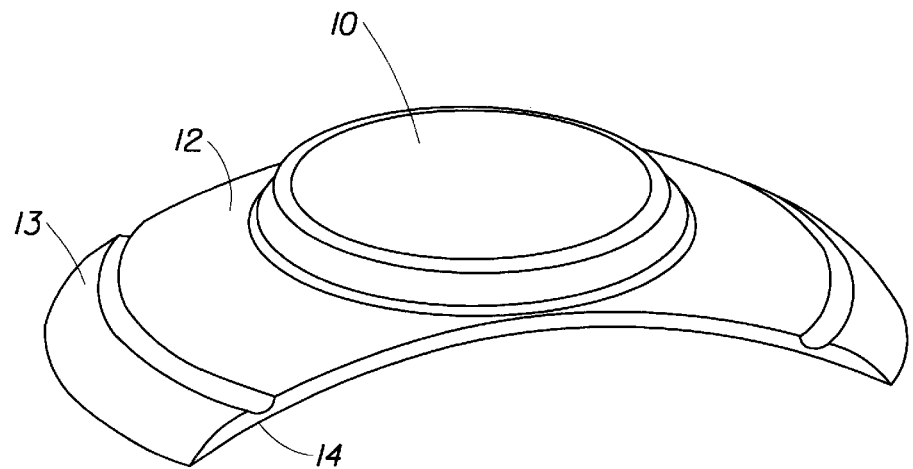

FIG. 9 has the same design feature as FIG. 6, except FIG. 9 has a positive optical body. FIG. 10 shows top perspective views of selected examples for FIG. 6 and FIG. 9. FIG. 13 shows the top perspective views of FIG. 11 and FIG. 12. FIG. 15 is the top perspective view of FIG. 14.

At least two objectives are achieved by this length adjustable design of the second portion of haptic body. First, when the second portion of the haptic body rests on the zonule flatly, it increases the contact area of the PRL with the neighboring eye tissue. Therefore, the PRL's weight and any residual stress caused by the oversized PRL now rests on and distributes into a much larger contact surface area created by the flattening of the second portion of the haptic body. Consequently, it reduces the local stress where haptics contact with surrounding tissue and, therefore, the PRL becomes more anatomically compatible than the ones shown in FIG. 2 or FIG. 3. Second, it prevents the oversized PRL from vaulting excessively towards the anterior chamber by reducing the effective length of the PRL by rolling at least part of the second portion of the haptic body into the sulcus (FIG. 8). Using the lenses of the present invention, the negative impacts caused by the excessively oversize length of a conventional PRL are reduced or eliminated.

When a cut, groove or score is incorporated into the transition zone, they may be made on either side (anterior or posterior) of the lens. For example, in FIG. 22, the groove is on the posterior side of the lens, while in FIG. 9, the groove is on the anterior side of the lens. The transition zone may also incorporate both a groove and a change in curvature from the first to the second haptic portions (see FIG. 22).

The first portion of the haptic body preferably has a constant width, generally in the range of from about 4 mm to about 8 mm, preferably about 5.5 mm to about 6.5 mm. The haptic width is preferably slightly larger than the diameter of the optical body. This way, when the iris contracts in strong light conditions, it will easily slide over the haptic body first, and then further continues to engage itself with the edge of the optical body as further iris contraction occurs.

The haptic portion of the lens (11) may have a relatively constant thickness throughout its length (see, for example, FIG. 19) or it may change in thickness. The most common version of this latter scenario is where the second haptic portion tapers in thickness from the transition zone to its outer edge (see FIGS. 20 and 21).

The lens itself may be made from materials conventionally used for preparing intraocular lenses. Such materials must have the durability, strength, optical clarity, refractive index and flexibility required for such a lens where the lens is formulated to float in the posterior chamber of the eye, the specific gravity and the mass/surface area ratio of the lens may also be considered. Examples, of materials which may be used in formulating the lenses of the present invention include silicones, silicone acrylate copolymers, polymethylmethacrylate (PMMA), hydrogels such as polyhydroxyethyl methacrylates, soft acrylic polymers, collagen/acrylate blends, collagen/hydrogel blends, and mixtures and copolymers thereof. A preferred material is silicone.

As is know to those skilled in the art, PMMA is a hard solid material which is well-suited for use in a PRL, which is made to be as thin as possible. When a PRL is made from PMMA or other hard acrylic materials, the haptics can be as thin as about 10 $\mu$m. At this thickness, the PMMA haptic is very flexible and can be bent easily without breaking. When the thickness of a PMMA haptic is about 70 $\mu$m, it begins to show a significant amount of flexibility. On the other hand, when a soft material, such as silicone, is used for the preparation of PRLs, the preferred haptic thickness is in the range of about 0.1 mm to about 0.3 mm. The thickness of the haptics is primarily determined by the flexibility or hardness of the material used to make the PRL. The harder the material, the thinner the haptics are made.

Figure 24A:
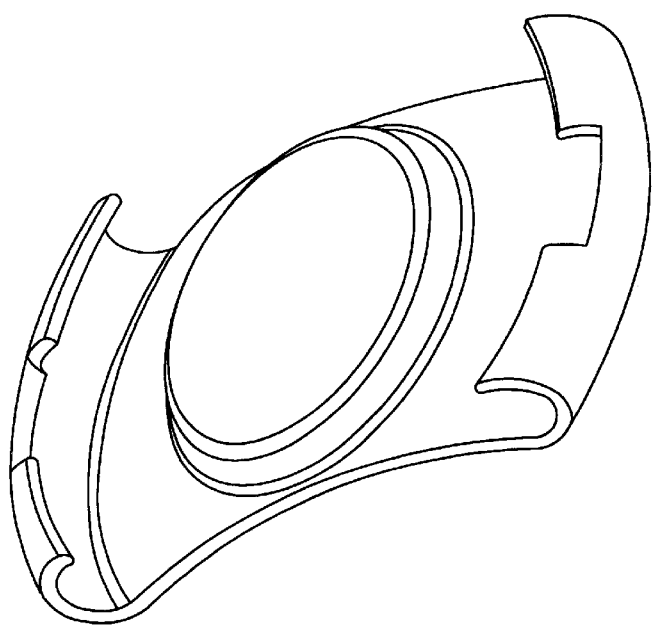
Figure 24B:
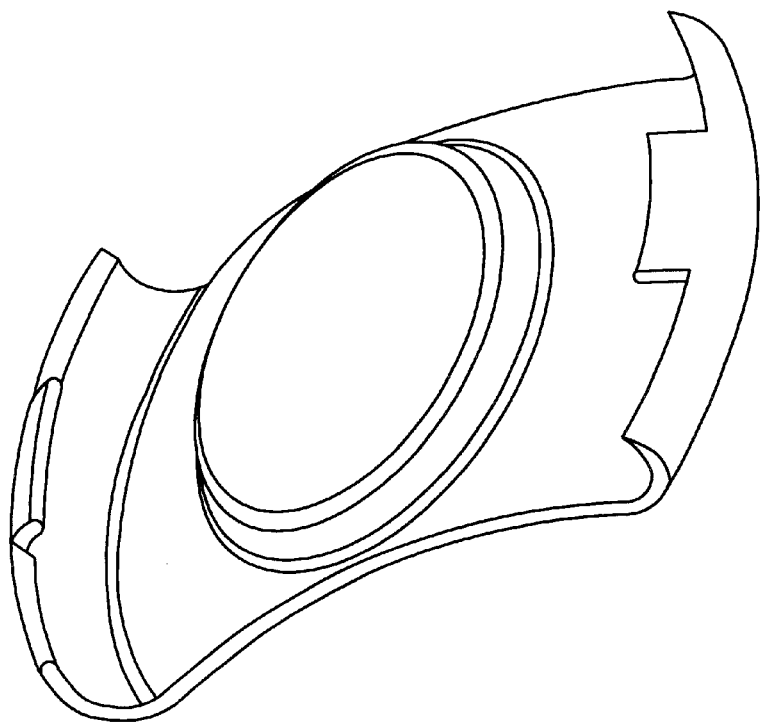
Figure 24C:
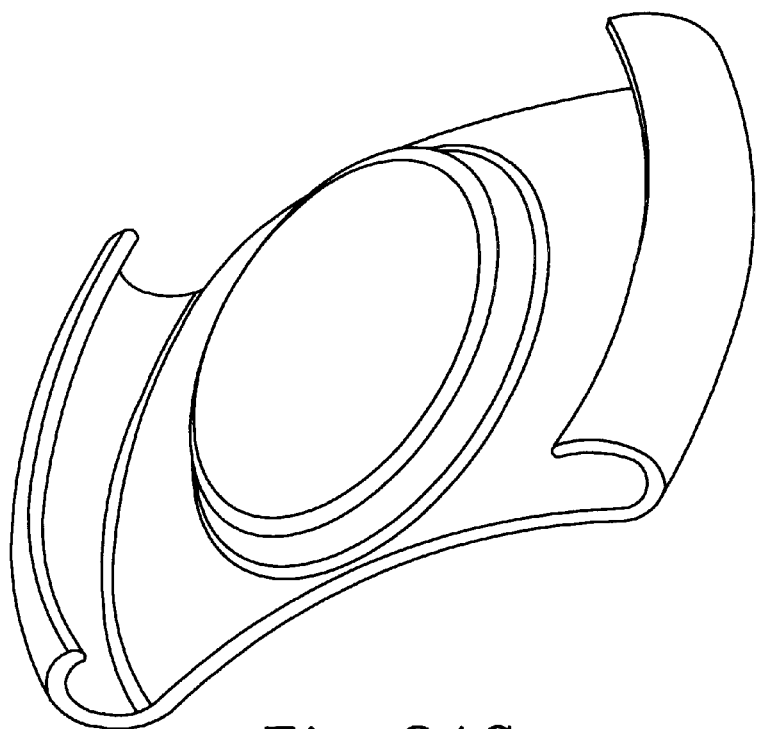
Figure 25A:
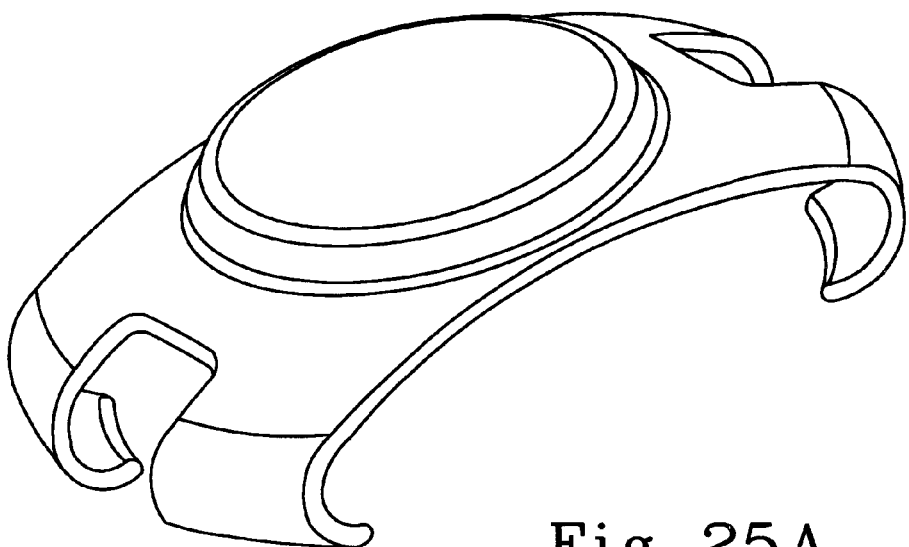
Figure 25B:
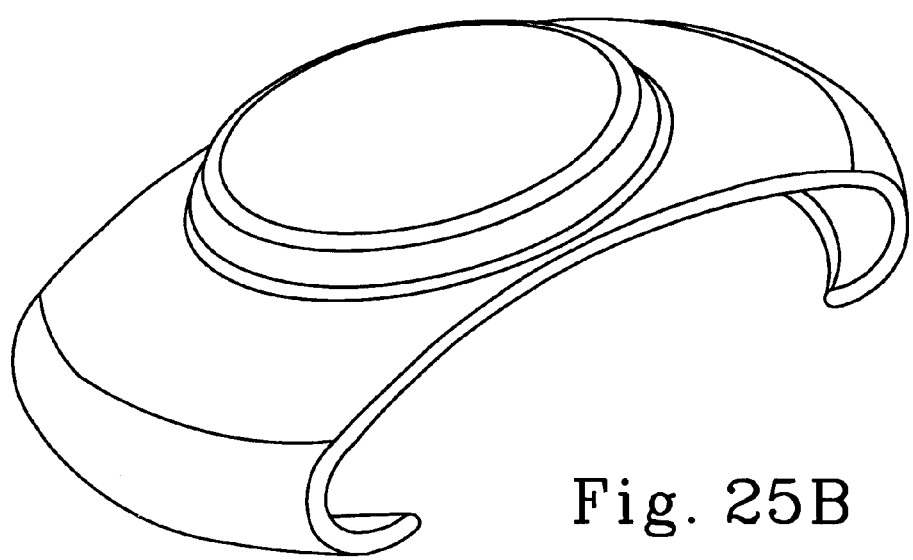
Figure 25C:
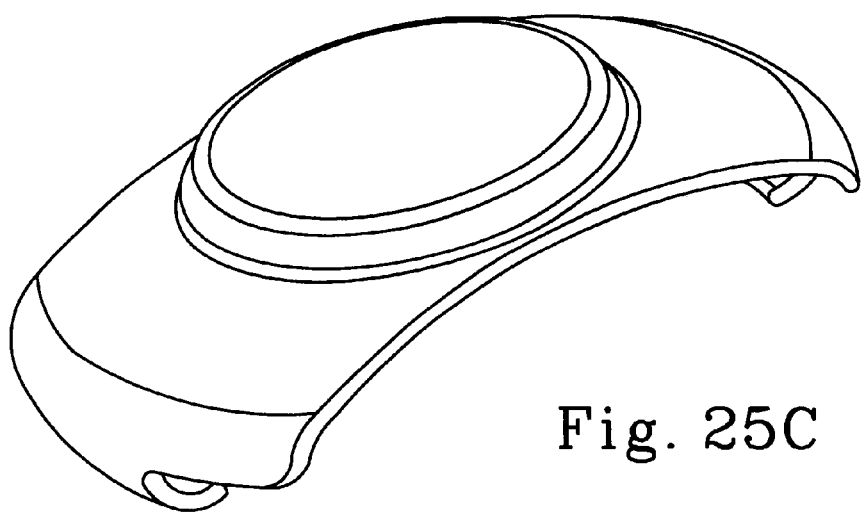
Figure 26:
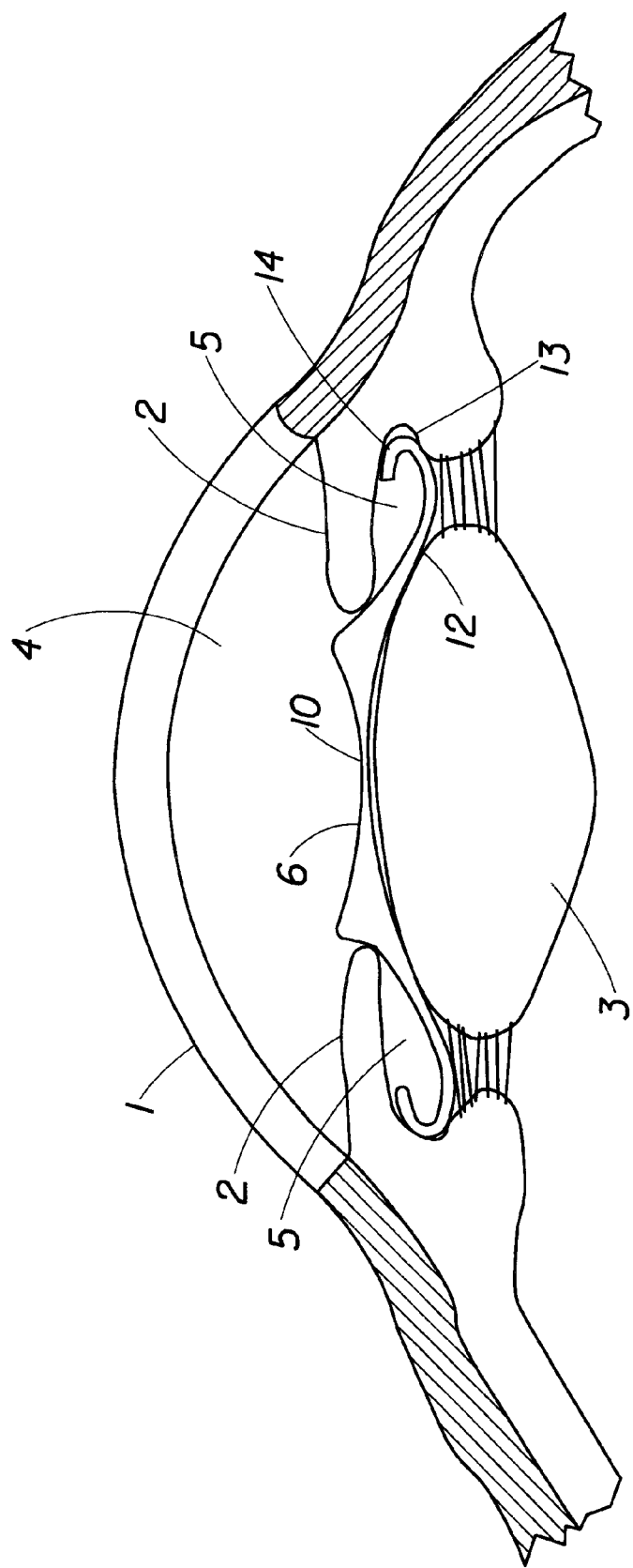
FIGS. 26 and 27 are schematic views of the structure of the eye showing the placement of PRL's of the present invention in the eye.
Figure 27:
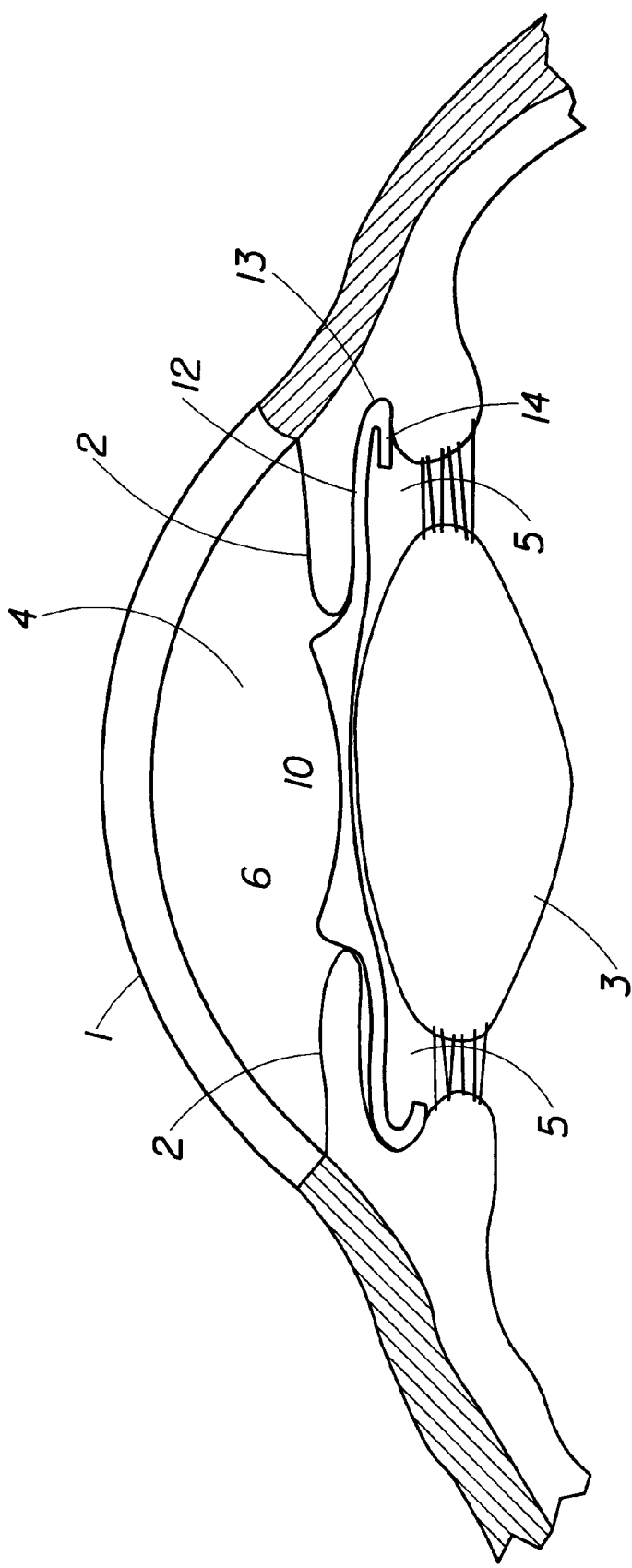

Additional examples of anatomically compatible, size adaptive PRL designs included within the present invention are illustrated in FIGS. 24 (A–C) and FIGS. 25 (A–C). In these examples, the optical body is designed for the correction of myopia with astigmatism or hyperopia with astigmatism. PRLs with these designs are positioned for sulcus fixation as shown, for example, in FIGS. 8, 26, and 27. The difference between FIG. 8 and FIG. 26 is that, in FIG. 8, part of the second portion of the haptic body is in a face-to-face contact with the zonule, while FIG. 26 has limited or no contact with the zonule. In both FIG. 8 and FIG. 26, the remainder of the second portion of the haptic body rolls into the sulcus.

Figure 28:
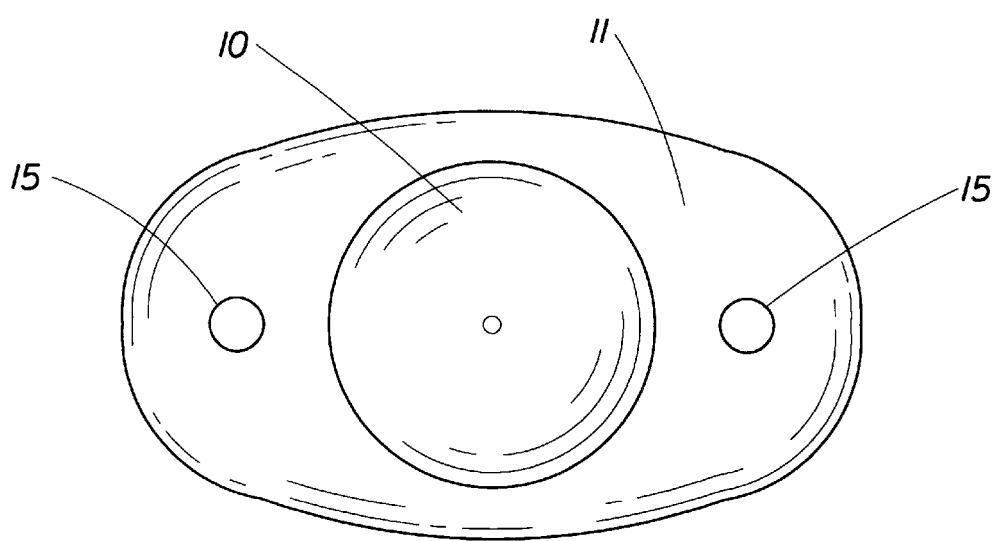
FIG. 28 is a top view of the prior art intraocular lens described in U.S. Pat. No. 5,913,898.
Figure 29A:
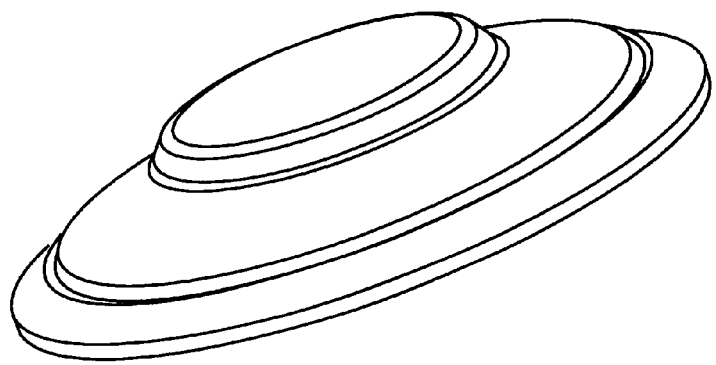
FIGS. 29–33 illustrate examples of circular lens versions of the present invention. They are analogous to various plate lens embodiments described in the present application
Figure 29B:
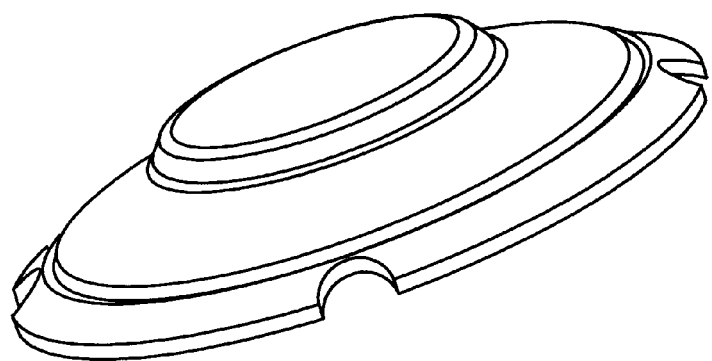
Figure 30:
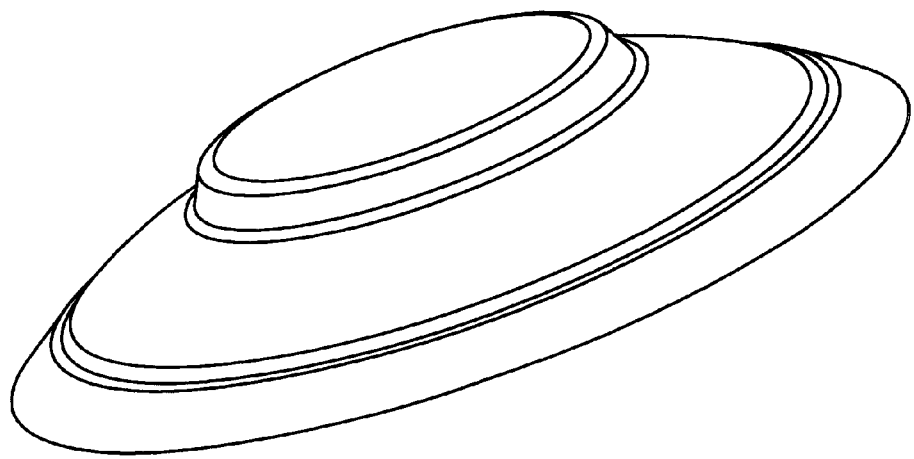
Figure 31:
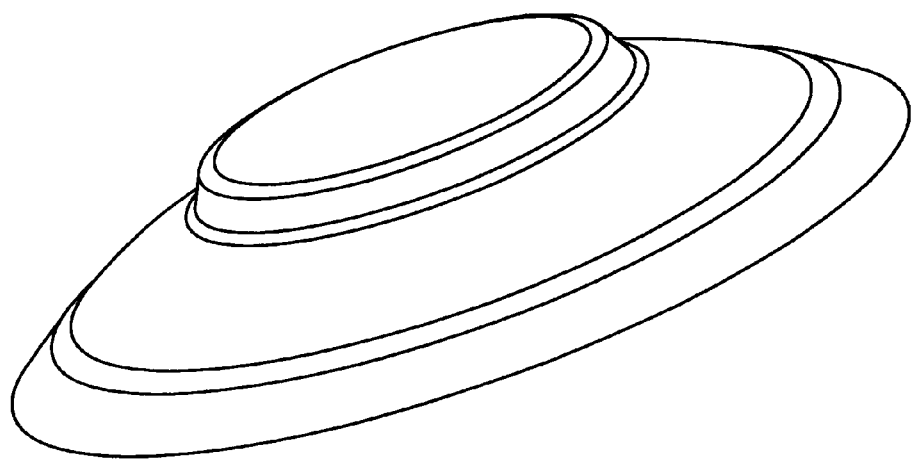
Figure 32A:
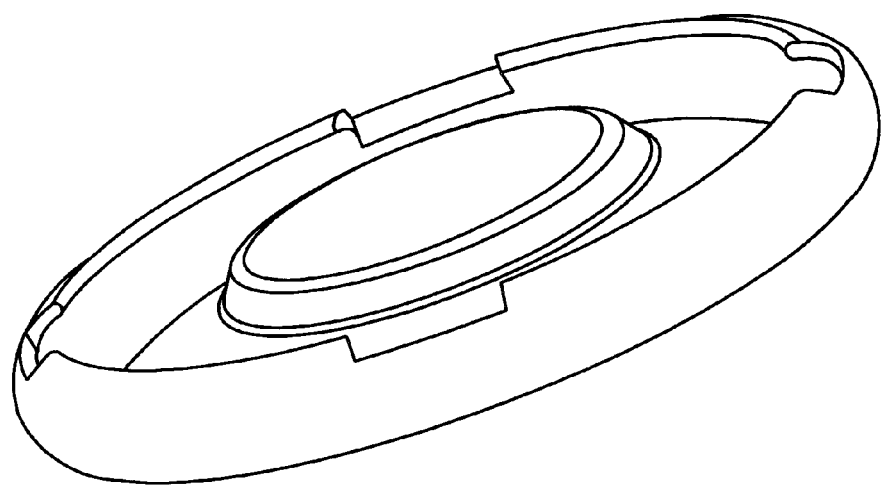
Figure 32B:
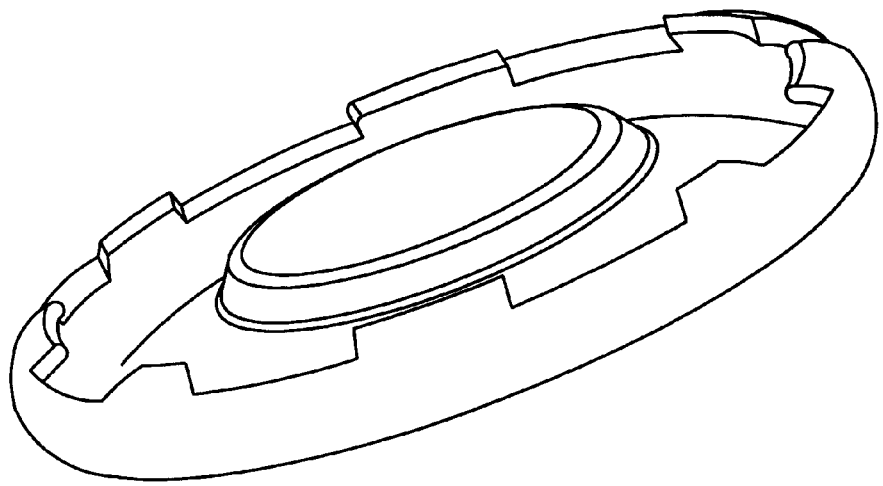
Figure 32C:
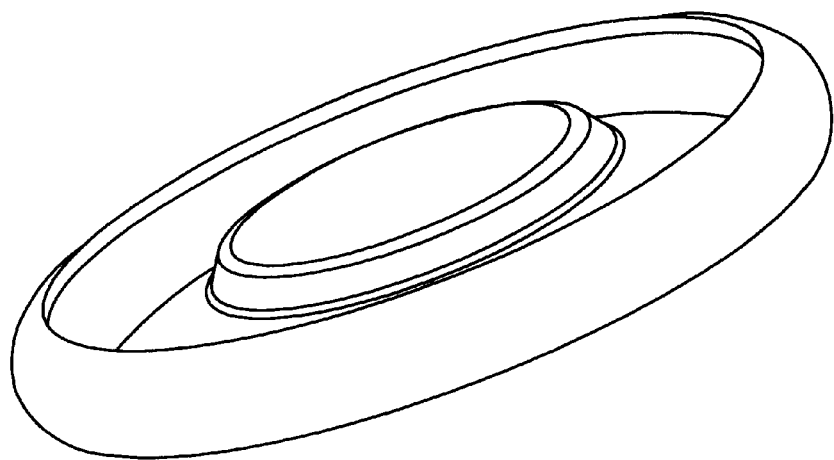
Figure 33A:
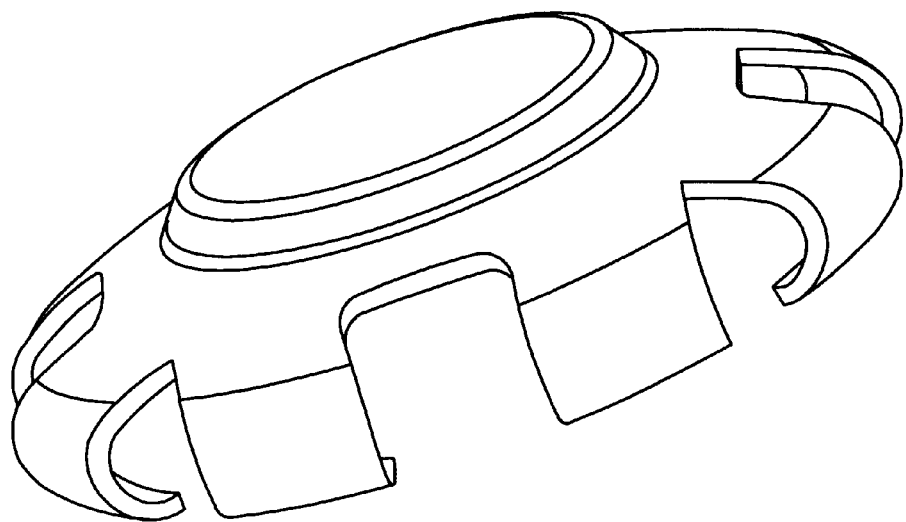
Figure 33B:
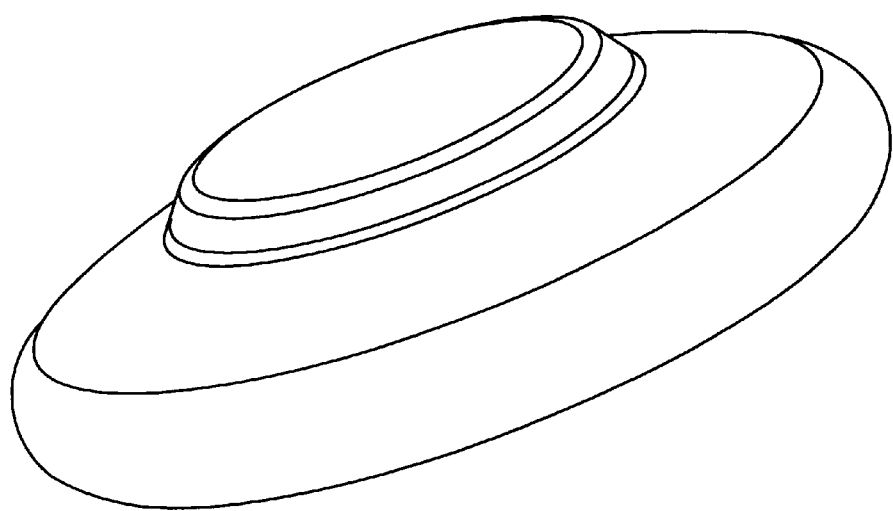
Figure 33C:
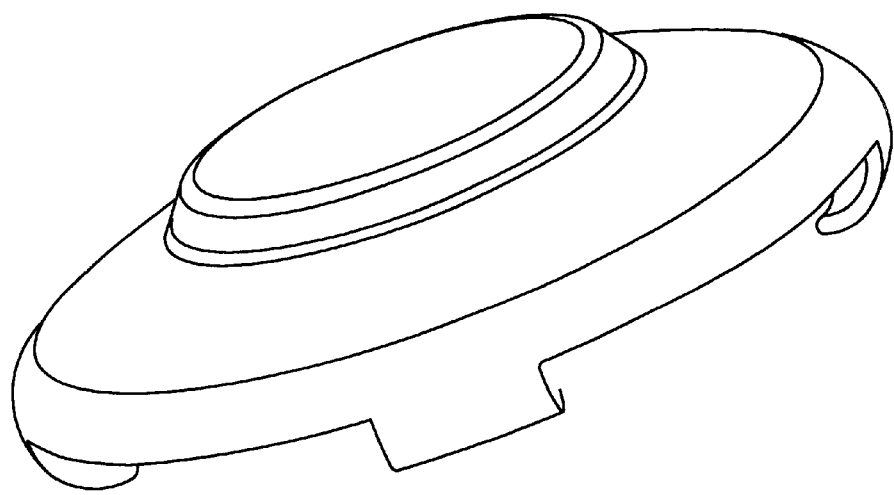

In addition to the anatomically compatible and size adaptive design, PRLs in FIGS. 24 (A–C) have another particularly useful feature: the curling structure at both ends of the haptic body (pre-curl), which allows a surgeon to manipulate the PRL with a simple tool. To position the PRL properly in the posterior chamber, a surgeon needs to place one haptic under the iris first, then tug in the second haptic under the iris. Often, this task is a challenge, especially for a new surgeon, for the following reasons. During the surgical procedure, surgeons should never directly touch the natural crystalline lens or exert a force downward along the eye axis against the natural crystalline lens. This is due to the high sensitivity of the natural crystalline lens to outside disturbing forces. Any direct touch or pushing down of the natural crystalline lens will cause progressive lens opacification, i.e., cataract formation. For the same reason, Feingold, in his U.S. Pat. No. 5,913,898, issued Jun. 22, 1999, discloses one or more indents (15), as shown in FIG. 28, on the haptic body for manipulating the lens inside the eye. Still, in Feingold's invention, a slight force downward against the natural crystalline lens is inevitable in order to manipulate the PRL. On the other hand, the curling (pre-curl) structure at both end of the haptic body in the present invention is the ideal design for pushing the haptics under the iris with a force toward the periphery of the natural crystalline lens. In other words, the pushing force for positioning the haptics is perpendicular to the eye axis. This way, both haptics can be pushed under the iris without applying a force downward against the natural crystalline lens.

Lastly, the present invention is particularly useful for PRLs designed for the correction of myopia with astigmatism or hyperopia with astigmatism. Astigmatism is the optical defect in which refractive power is not uniform in all meridians. To successfully correct astigmatism, the PRL cannot be rotated randomly inside the eye. In other words, the PRL must maintain a certain orientation in relationship with the eye. Designs of the present invention provide a means for achieving the fixated orientation of the PRL once implanted into the eye.

One preferred embodiment of the present invention is shown in FIG. 6. In this design, the optical body has a diameter of about 3 to about 7 mm, preferably about 4.5 to about 5.5 mm. The posterior surface of the optical body conforms substantially to the anterior surface of the capsule of the human eye. The radius of curvature of the posterior surface of the optical body is from about 8 mm to about 12 mm, preferably from about 9.5 mm to 10.5 mm. The anterior surface of the optical body can be concave (FIG. 6) or convex (FIG. 9) depending on whether it is a negative PRL for myopic patients or positive PRL for hyperopic patients. The central lens thickness of the optical body for the negative PRL should be as thin as possible, preferably in the range of from about 0.01 mm to about 0.3 mm. The edge thickness of the optical body for the negative PRLs varies based on the optical power of the lens and can be calculated from standard optical equations, given the diameter of the optical body, and the refractive indices of the lens material and the media. Nevertheless, the edge thickness preferably does not exceed about 1 mm. The first portion of the haptic body has a diameter ($L_1$) of from about 8 mm to about 11 mm, preferably from about 9 mm to about 10 mm. The V-shape cut is located in the zone defined by the diameters between about 8 mm and about 11 mm, preferably between about 9 mm and about 10 mm. The second portion of the haptic body starts where the V-shape cut ends, anywhere in a zone defined by the diameters ($L_2$) between about 8 and about 11 mm, preferably between about 9 mm and 10 mm. The overall diameter of the second haptic body is from about 11 mm to about 14 mm.

A more specific preferred embodiment is the same PRL design shown in FIG. 6 with an optical diameter of about 5 mm. It has a diagnostic diameter of the first portion of the haptic body ($L_1$) of about 9 mm, the V-shape cut in the zone defined between the diameters of about 9 mm and 10 mm, and the diagnostic diameter of the second portion of the haptic body ($L_2$) of about 13 mm. In order to understand how this PRL design fits in eyes of various sizes, the following four scenarios are analyzed for the purpose of illustration.

Figure 1:
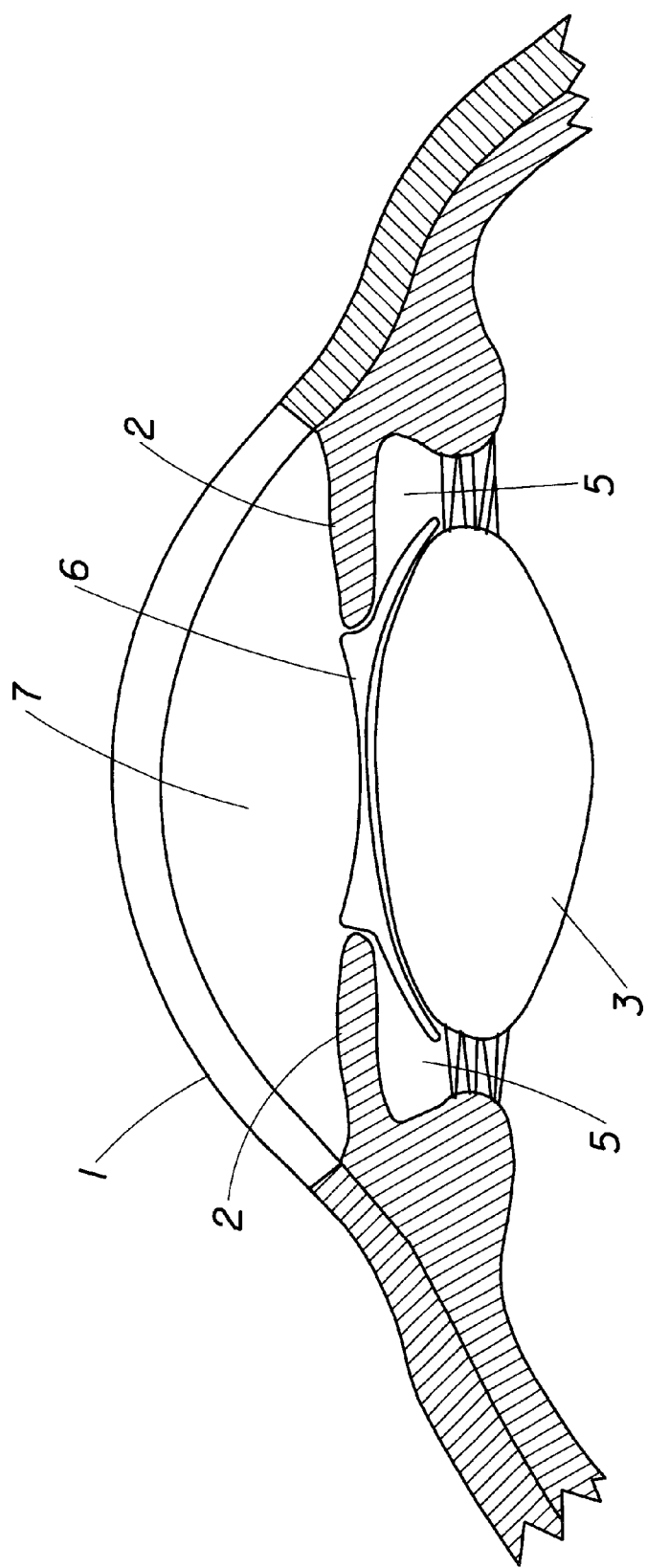
FIG. 1 is a schematic view of the structure of the eye showing the placement of a PRL.

Scenario 1: The PRL is smaller than the natural crystalline lens. It is extremely unlikely that any patient's natural crystalline lens has a diameter larger than 13 mm. Nevertheless, the PRL of the present invention in this scenario will be simply positioned on the anterior surface of the capsule, as it is shown in FIG. 1 (the V-shape cut on the PRL is not shown in FIG. 1).

Scenario 2: The PRL has the same size as the natural crystalline lens. In this scenario, the PRL just fits on the natural crystalline lens. The position of the PRL inside the eye is similar to that in FIG. 1, except that the edge of the second portion of the haptic body may barely touch the zonules.

Figure 2:
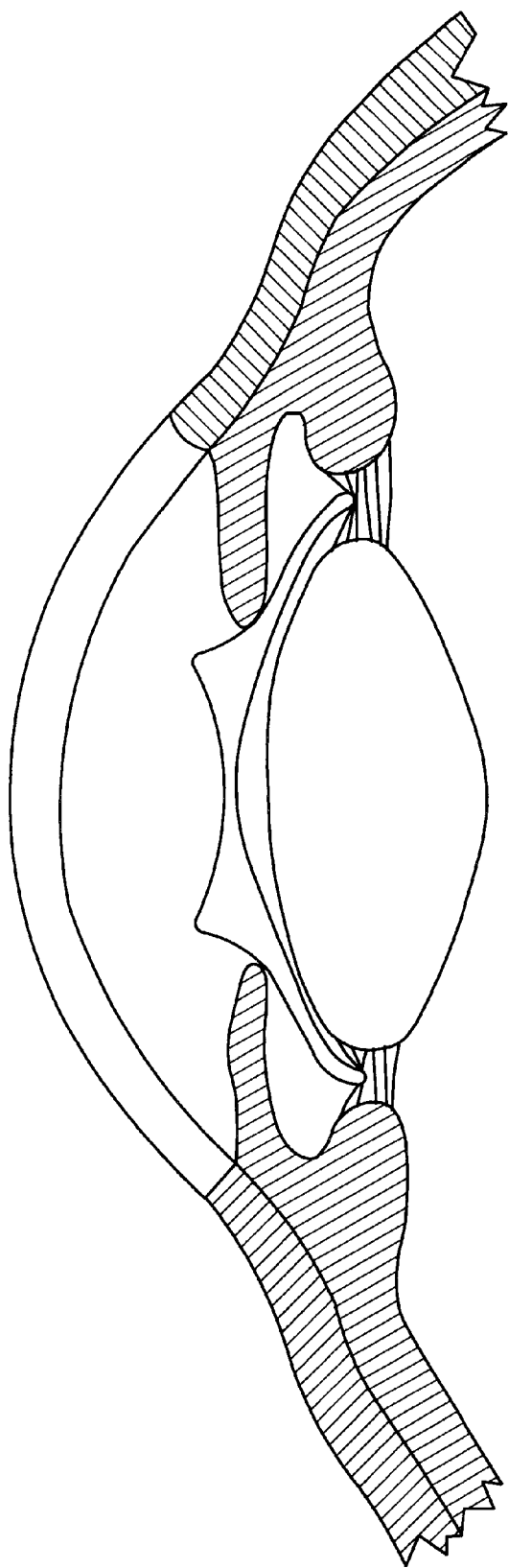
FIGS. 2 and 3 are schematic views of the structure of the eye showing the placement of a PRL which is too large for the particular eye shown.

Scenario 3: The PRL is larger than the natural crystalline lens but smaller than the sulcus-to-sulcus distance. In this situation, the second portion of the haptic body is long enough to flatly rest on the zonules but not long enough to curl or roll into the sulcus. In this scenario, part or all of the second portion of the haptic body rests flatly on the zonules (FIG. 7). As a result, the contact area between the haptic body and zonules is increased, thereby reducing the local stress points which otherwise may exist (FIG. 2).

Figure 3:
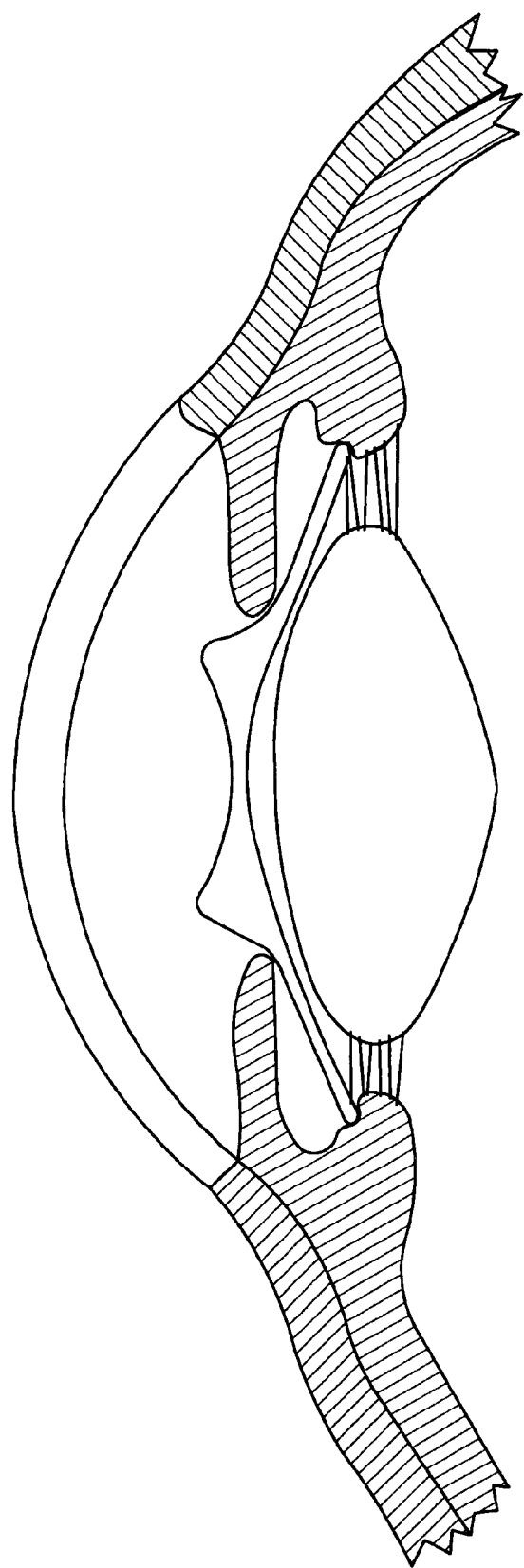
Figure 4A:
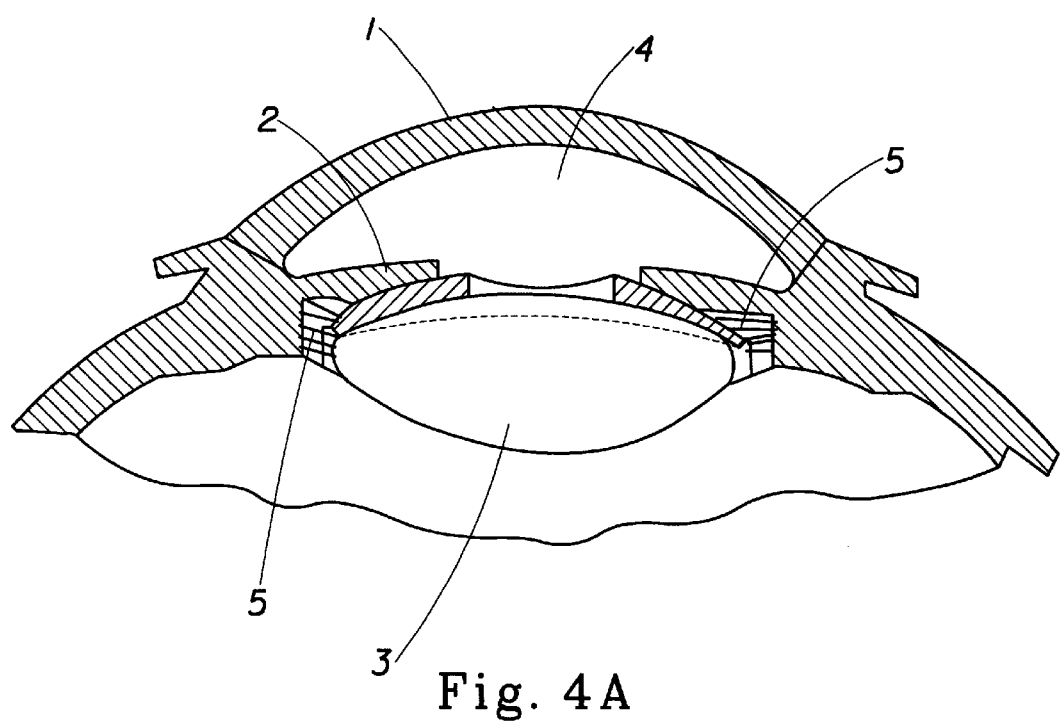
FIG. 4 is a top view of a prior art non-floating intraocular lens (U.S. Pat. No. 5,258,025) and a schematic view showing the placement of that lens in the eye.
Figure 4B:
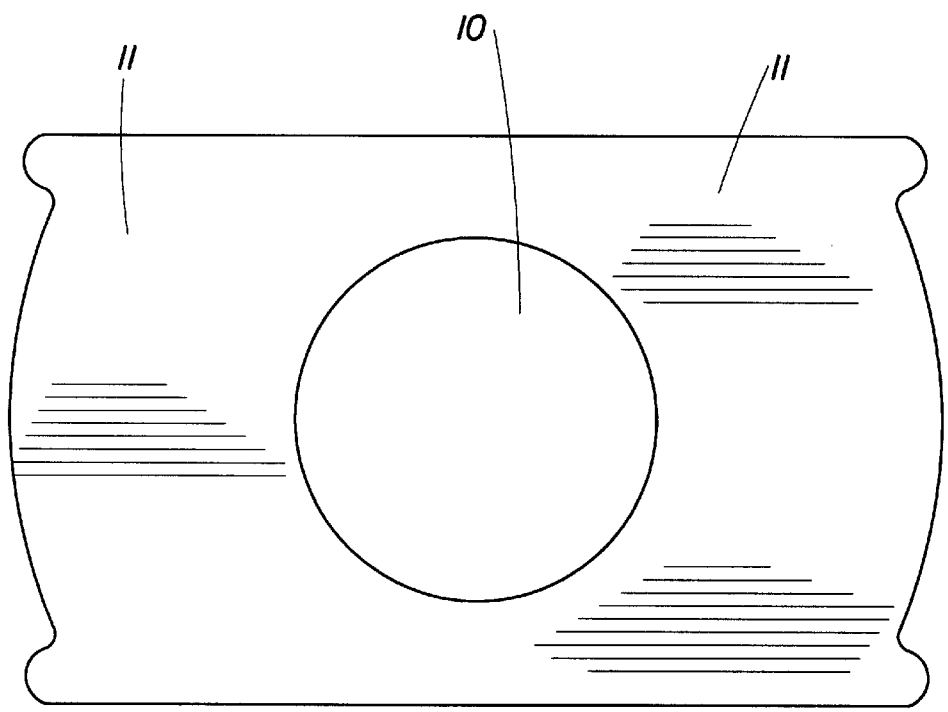
Figure 5:
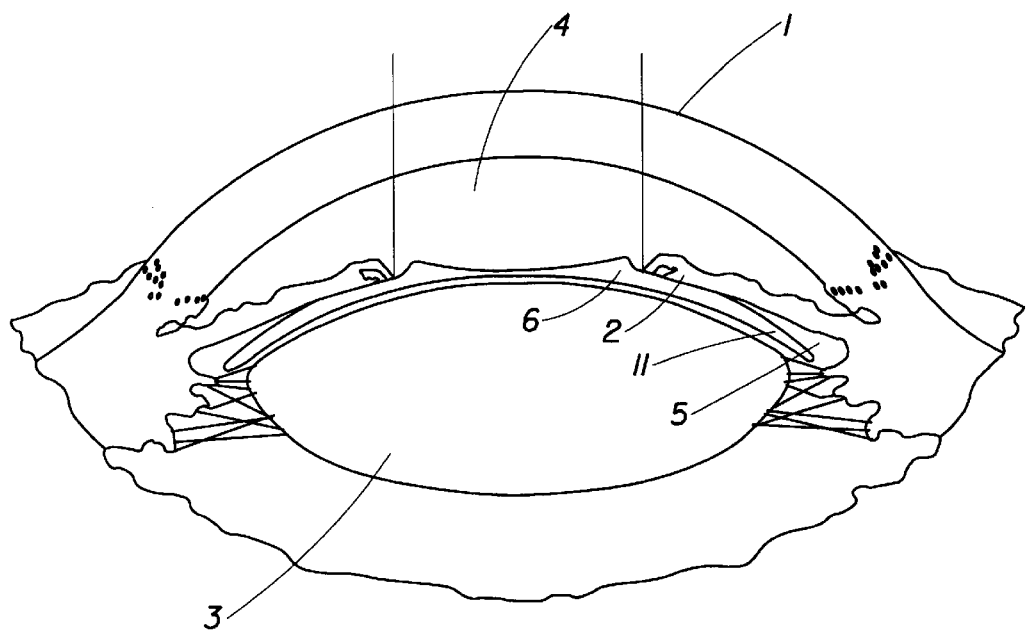
FIG. 5 is a schematic view showing the placement of a prior art floating intraocular lens (U.S. Pat. No. 6,015,435) in the eye.

Scenario 4: The PRL is so long that part of the second portion of the haptic body rests on zonules and rest of the second portion of the haptic body curls and rolls into the sulcus (FIG. 8). This curling and rolling motion reduces the effective overall length of the PRL. This prevents excessive vaulting which otherwise may exist (FIG. 3).

Additional preferred embodiments for PRL designs in the present invention are illustrated in FIG. 24. In these designs, the optical body has a diameter of from about 3 mm to about 7 mm. The first portion of the haptic body has a diagnostic diameter ($L_1$) in the range of from about 8 mm to about 11 mm. The curvature of the posterior surface of the first portion of the haptic body is preferably substantially the same as that of the optic body, having a radius of from about 8 mm to about 12 mm. The second portion of the haptic body has an effective overall length ($L_2$) in the range of from about 11 mm to about 14 mm. Between the first and second portions of the haptic body, there is a transition zone where the curvature of the first portion of the haptic body starts to gradually change to the second curvature for the second portion of the haptic body.

An even more preferred embodiment is the one shown in FIG. 24–C with an optical diameter of about 5 mm, a diameter of the first portion of the haptic body of about 9 mm to about 10 mm. The transition zone is in the continuous blending area where the curvature of the first portion of the haptic body gradually changes to the curvature of the second portion of the haptic body. The second portion of the haptic body is extended from the first portion of the haptic body and is curled with an overall diameter of from about 12 mm to about 14 mm. The effective overall length is purposely designed to be in excess of the sulcus-to-sulcus distance of an average patient's eye. The excess part of the second portion of the haptic body rolls into the sulcus until the effective overall length of the PRL fits the patient's eye size without substantial vaulting towards the anterior chamber (FIG. 26).

Those who are skilled in the art understand that hyperopic patients usually have smaller eye dimensions than myopic patients. The dimensions for the haptic body disclosed in above paragraphs are most suitable for myopic patients. In general, that the haptic lengths discussed in above paragraphs are reduced by about 0.5 mm up to about 1.5 mm when used in hyperopic patients.

We claim:
1. An anatomically compatible phakic refractive lens for the correction of ametropia, structurally adapted to be positioned in the posterior chamber of the eye, comprising:
(a) an optical body having a diameter of from about 3 mm to about 7 mm; and
(b) at least one haptic body which comprises:
(i) a first portion which is attached to and extends from said optical body, has a diagnostic distance of from about 8 mm to about 11 mm, and which is structurally adapted to conform in whole or in part to the anterior surface of the natural crystalline lens of the eye;

(ii) a second portion which extends outward from the outer edge of said first portion, and has a diagnostic distance of from 11 mm to about 14 mm; and (iii) a transition zone between said first portion and said second portion structurally adapted to permit said second portion to conform to the shape of the ciliary sulcus of the eye.

2. The lens according to claim 1 wherein the posterior surface of the first haptic portion has substantially the same radius of curvature as the posterior surface of the optical body.

3. The lens according to claim 2 which comprises two haptics extending in opposite directions from the optical body.

4. The lens according to claim 3 which includes one or more of the following features in the lens surface: score, groove, cut, and change in the radius of curvature or slope of the posterior surface of the haptic.

5. The lens according to claim 4 wherein the second haptic portion bends relative to the first haptic portion.

6. The lens according to claim 5 made from a material selected from silicones, silicone acrylate copolymers, polymethyl methacrylates, hydrogels collagen/acrylate blends, collagen/hydrogel blends, and mixtures and copolymers thereof.

7. The lens according to claim 6 wherein the diagnostic distance of the first haptic portion is from about 9 to about 10 mm.

8. The lens according to claim 7 wherein the diagnostic distance of the second haptic portion is from about 12 to about 13.5 mm.

9. The lens according to claim 8 wherein the optical body has a diameter of from about 4.5 to about 5.5 mm.

10. The lens according to claim 9 wherein the transition zone includes a V-shaped groove along its width.

11. The lens according to claim 6 wherein the transition zone includes a V-shaped groove along its width.

12. The lens according to claim 11 made from silicone.

13. The lens according to claim 12 wherein the haptic body has a thickness of from about 0.1 mm to about 0.3 mm.

14. The lens according to claim 11 made from PMMA.

15. The lens according to claim 14 wherein the haptic body has a thickness of from about 10 $\mu$m to about 70 $\mu$m.

16. The lens according to claim 6 wherein the second haptic portion tapers in thickness toward its outer edge.

17. The lens according to claim 6 wherein the second haptic portion is pre-curled relative to the first haptic portion.

18. The lens according to claim 1 which corrects for astigmatism.

19. The method for implanting a phakic refractive lens in an eye comprising the step of surgically inserting the lens according to claim 1 into the posterior chamber of the eye such that the second portion of the haptic body is located in and conforms to the shape of the ciliary sulcus of the eye.

* * * * *